United States Patent [19]

Chand

[11] Patent Number: 4,498,970
[45] Date of Patent: Feb. 12, 1985

[54] ELECTROCHEMICAL GAS SENSOR

[75] Inventor: Ramesh Chand, Woodland Hills, Calif.

[73] Assignee: GC Industries, Chatsworth, Calif.

[21] Appl. No.: 383,145

[22] Filed: May 28, 1982

[51] Int. Cl.³ .................... G01N 27/30; G01N 27/54
[52] U.S. Cl. .................................................. 204/415
[58] Field of Search ............... 204/415, 403, 1 P; 128/635

[56] References Cited

U.S. PATENT DOCUMENTS

| | | | |
|---|---|---|---|
| 3,429,796 | 2/1969 | Lauer | 204/415 |
| 3,510,420 | 5/1970 | Mills | 204/415 |
| 3,708,412 | 1/1973 | Lofgren | 204/415 |
| 4,132,616 | 1/1979 | Tantram et al. | 204/415 |

FOREIGN PATENT DOCUMENTS 1442303  7/1976  United Kingdom ............... 204/415

*Primary Examiner*—G. L. Kaplan
*Attorney, Agent, or Firm*—Fulwider, Patton, Rieber, Lee & Utecht

[57] ABSTRACT

An electrochemical gas sensor having a relatively small sensing electrode (12) formed from powdered metal pressed onto a relatively thick porous sheet (24) of polytetrafluoroethylene (PTFE), through which gas is diffused. The electrode (12) is located at one end of a housing (10) containing an electrolyte (22) and a counter electrode (14). The sensing electrode structure provides relative insensitivity to temperature changes, rapid response to pressure charges, and a desirably low operating current.

5 Claims, 1 Drawing Figure

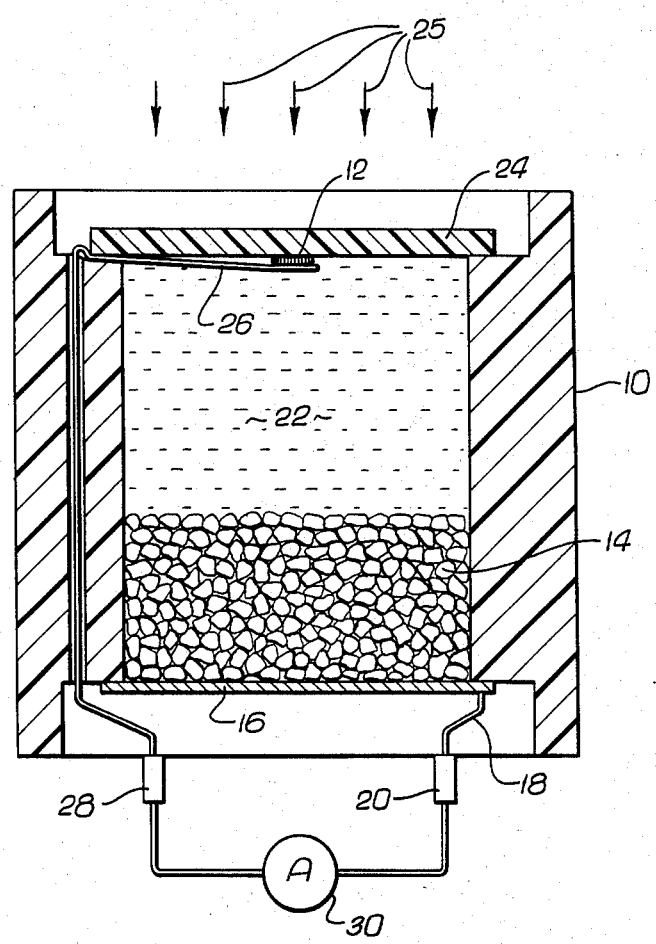

ELECTROCHEMICAL GAS SENSOR

BACKGROUND OF THE INVENTION

This invention relates generally to electrochemical gas sensors, and, more particularly, to an improved sensing electrode structure for electrochemical gas sensors. Gas sensors of this type are used to measure the partial pressure of a gas in a mixture of gases. For example, by appropriate selection of components, a gas sensor can indicate the concentration of oxygen in air. Other sensors indicate the concentrations of carbon monoxide, sulfur dioxide, oxides of nitrogen, hydrogen sulfide, and various other gases.

Basically, an electrochemical gas sensor of the type with which the invention is concerned includes a container in which there are disposed an electrolyte, a sensing electrode, and a counter electrode. When a gas to be sensed is introduced into the electrolyte adjacent to the sensing electrode, ions are formed and act as current carriers. A measureable current can then be detected in an external circuit connected to the electrodes.

There are two basic categories of sensors of this general type. One is the galvanic type, in which the counter electrode and electrolyte are selected to provide a measureable current without any external voltage source being necessary. For example, the use of lead or cadmium as a counter electrode, in an alkaline electrolyte, provides a galvanic sensor for the measurement of oxygen concentration. Also, the use of lead dioxide or manganese dioxide as the counter electrode, in an acid electrolyte, provides a galvanic sensor for the measurement of concentrations of carbon monoxide, hydrogen sulfide, and sulfur dioxide. The other type of sensor is referred to as the polarographic type, in which the counter electrode is of such a nature as to require the use of an external voltage source to make the sensor operate. The magnitude of the required external voltage will depend on such factors as the nature of the counter electrode, the acidity (pH) of the electrolyte, and the gas to be measured. The present invention is not limited to either the galvanic or the polarographic type of sensor.

An important consideration in one application of gas sensors is that the readings obtained should be proportional to the partial pressure of the gas to be measured. For example, in monitoring the partial pressure of oxygen in air for health reasons, the reading should reflect changes in total air pressure, even though the oxygen concentration may not have changed. In other words, the sensor should be indicative of the total amount of oxygen available, which is proportional to partial pressure, rather than indicative of the concentration of oxygen by weight or volume.

A typical oxygen-sensing device of the prior art is described in U.S. Pat. No. 3,429,796, issued in the name of Jay M. Lauer. The sensing electrode in the Lauer device is a metallic mesh on which has been deposited a layer of silver or gold. The gas to be measured is introduced through a membrane of solid Teflon (DuPont) having a thickness of 0.001 to 0.002 inch. Typically, sensors of this type have sensing electrodes of about one-inch diameter, and generate currents in the range of 200 to 1,000 microamperes. The current is a measure of the useful life of the sensor. A lower operating current will result in a longer useful life. Sensors of this type are also very temperature dependent, since the gas has to permeate through a non-porous membrane. Temperature variations may result in readings differing by as much as 5-10% per degree C. In addition, the thin membrane renders the device very fragile and susceptible to electrolyte leaks.

Another sensor is described in U.S. Pat. No. 4,132,616, issued in the names of Anthony D. S. Tantram et al. In the Tantram device, the sensing electrode is approximately 0.5 inch in diameter and is made of nickel gauze pressed onto a porous Teflon tape of about 0.008 inch thickness. Between the Teflon and the gas sample is a plug with a capillary to reduce the flow of gas to the sensing electrode. However, the operating current level is still at approximately the 1,000 microampere level, thus significantly limiting the useful life of the device. In addition, the capillary arrangement renders the sensor insensitive to changes in partial pressure, and is therefore not suitable for human safety applications.

It will be appreciated from the foregoing that there is still a significant need in the gas sensing field for an electrochemical gas sensor that overcomes the problems of the prior art. In particular, what is needed is a sensor with a relatively low working current, to provide a long useful life, insensitivity to temperature variations, and the ability to respond relatively quickly to changes in partial pressure of the sensed gas. The present invention satisfies these requirements.

SUMMARY OF THE INVENTION

The present invention resides in an electrochemical gas sensor with an improved sensing electrode structure that results in a low working current, low sensitivity to temperature variations, and rapid response to changes in the partial pressure of the sensed gas. In addition, the sensor of the invention is sturdy in construction, and less susceptible to damage than some sensors of the prior art.

Briefly, and in general terms, the gas sensor of the invention includes a container, an electrolyte and a counter electrode similar in nature to those found in other devices of this type. However, the invention differs in the structure of its sensing electrode, which is formed from a powdered metal pressed into a bond with a relatively thick porous sheet of polytetrafluoroethylene (PTFE) material, such as Teflon (DuPont). The diameter of the sensing electrode is considerably smaller than those of the prior art, and the resulting structure provides a working current in the range of 100-200 microamperes, and a correspondingly long useful life.

In terms of a novel method of making a sensing electrode, the invention comprises the steps of mixing powdered metal, such as platinum, with a PTFE dispersion, adjusting the acidity of the mixture, and pouring it over filter paper, on which the metal is allowed to settle. The remaining steps include etching one surface of a sheet of PTFE, pressing a portion of the filter paper and metal powder into the etched surface, then removing the filter paper and bonding a contact wire onto the powdered metal electrode.

It will be appreciated from the foregoing that the present invention represents a significant advance in the field of electrochemical gas sensing. In particular, the provision of a sensing electrode of small area, bonded to a thick porous Teflon sheet, results in a small working current and other desirable characteristics. Other aspects and advantages of the invention will become apparent from the following more detailed description, taken in conjunction with the accompanying drawings.

BRIEF DESCRIPTION OF THE DRAWING

FIG. 1 is a simplified sectional view of an electrochemical gas sensor incorporating the improvement of the present invention.

DESCRIPTION OF THE PREFERRED EMBODIMENT

As shown in the drawing for purposes of illustration, the present invention is principally concerned with improvements in electrochemical gas sensors. In the past, such sensors have typically yielded a relatively high operating current (above 1,000 microamperes), and a correspondingly short useful life. Prior sensors have also suffered from a high sensitivity to temperature variations, and were either non-responsive or only slowly responsive to changes in the partial pressure of the gas being measured.

In accordance with the present invention, a gas sensor is provided with a novel sensing electrode structure, which results in a relatively low operating current (100 to 200 microamperes), low sensitivity to temperature changes, and rapid response to partial pressure changes. In addition, the sensor of the invention is sturdily constructed, and therefore is not as susceptible to damage as some of its earlier counterparts.

As shown in FIG. 1, the gas sensor of the invention includes a generally cylindrical body, indicated by reference numeral 10, which may be conveniently formed from a plastic, such as polyvinylchloride, a sensing electrode 12, and a counter electrode 14. A contact plate 16 for the counter electrode forms a bottom closure for the sensor body 10, and also provides one external electrical contact, through a connecting wire 18 to a terminal 20. The counter electrode in the illustrative example is formed from lead particles of 40 to 100 mesh size, compressed against the plate 16, which may be of stainless steel. Typically, about ten grams of lead particles provide an operating life of twelve months. A suitable electrolyte 22 fills the sensor body 10, and the sensing electrode 12 is positioned at the top of the body.

Closing the top of the cylindrical sensor body 10 is a relatively thick sheet 24 of porous polytetrafluoroethylene (PTFE) material, such as Teflon (DuPont), preferably about 0.050 to 0.060 inch thick, with a pore size of 2-10 microns. The upper surface of the sheet 24 is exposed to a gas sample being analyzed, as indicated by the arrows 25. The sensing electrode 12 takes the form of a small area of powdered metal impregnated by the application of pressure into the sheet 24. For most applications, the sensing electrode 12 need only be 0.020 to 0.050 inch in diameter for proper operation. As usual, the sensing electrode should be of a noble metal, such as gold or platinum. A connecting wire 26, preferably of platinum, is bonded to the electrode 12, and connected at its other end to a second outside terminal 28. As shown, an ammeter 30 is usually connected across the terminals 20 and 28 to obtain a measure of the partial pressure of the gas being monitored.

Since the sheet 24 is about fifty times thicker than a Teflon membrane used in other sensors, the device is extremely sturdy in construction. The porosity of the sheet 24 renders the sensor rapidly responsive to changes is partial pressure. A ninety-percent change in pressure is sensed in less than ten seconds. However, the relatively small sensing electrode keeps the resultant currents to between 100 and 200 microamperes. Furthermore, the sensor of the invention is much less sensitive to temperature than others of its type. In the illustrative example, the sensor readings vary only about 1% per degree C.

The following is a detailed example of the steps used to fabricate the sensing electrode 12 in combination with the sheet 24. It will be understood that the example is not intended to limit the scope of the invention.

EXAMPLE

Three grams of fuel-cell grade platinum black powder (Englehard Industries) was stirred with 200 ml of water in a beaker. To this mixture was added two grams of Teflon 30 dispersion (duPont) and the resulting mixture was stirred vigorously for two minutes. The pH level of the solution was adjusted to 11.0 by the addition of 1N potassium hydroxide (KOH) solution. This mixture was then poured over a filter paper (Whatman #50), and the platinum powder was allowed to settle over the filter paper.

In preparing the sheet 24, a Teflon sheet 0.060 inch thick (Chemplast, Model 160) was etched on one side by the application of a Teflon treating agent (Chemgrip, manufactured by Chemplast) for one minute. The sheet was then washed successively in acetone, methanol, and distilled water, and then dried in an oven at 200 degrees F. A circular portion of this sheet 0.5 inch in diameter was cut using a suitable die.

A small piece, approximately 0.050 inch diameter, of the filter paper and platinum powder combination was placed in the middle of the etched surface of the Teflon sheet, with the platinum powder in contact with the Teflon. The whole assembly was pressed between flat platters to a pressure of 0.5 ton per square inch. Then the pressure was released and the filter paper gently removed with a fine tweezer. The Teflon and platinum assembly was pressed again to a pressure of 1.0 ton per square inch for one minute.

The pressed assembly was removed and dried in an oven at 200 degrees F. A platinum wire of 0.010 inch diameter and 2.0 inch length was then attached to the platinum powder by means of gold epoxy (Zinmex). The epoxy was cured at 400 degrees F. for two hours, after which the assembly was ready for installation in the sensor, by sealing the Teflon sheet to the sensor body with a Teflon epoxy.

It will be appreciated from the foregoing that the present invention represents a significant advance in the field of electrochemical gas sensing. In particular, the invention provides a sensing electrode structure that results in low current drain from the device, low sensitivity to temperature changes, and rapid response to changes in the partial pressure of the gas being measured. It will also be appreciated that, although a specific embodiment of the invention has been described in detail for purposes of illustration, various modifications may be made without departing from the spirit and scope of the invention. Accordingly, the invention is not to be limited except as by the appended claims.

I claim:
1. An electrochemical gas sensor, comprising:
a sensor body with a hollow interior;
an electrolyte filling said body;
a counter electrode disposed at one end of the interior of said body;
a sheet of porous material forming a closure at the other end of the interior of said body, and having an inner surface in contact with said electrolyte and an outer surface that is exposed to a gas sample for analysis;

a sensing electrode in the form of a relatively small area of powdered metal impregnated into the inner surface of said sheet by the application of pressure; and a pair of wires for making contact with said sensing electrode and said counter electrode, respectively, to measure a current between said electrodes generated as a result of the diffusion of gas into said electrolyte through said porous sheet;

whereby said porous sheet ensures that gas diffuses into said electrolyte rapidly enough to yield insensitivity to temperature and a rapid response to pressure changes, but the relatively small area of said sensing electrode results in a relatively small electrical current and a correspondingly long useful life;

and wherein said sheet of porous material is approximately 0.050 to 0.060 inch thick, approximately 0.5 inch in diameter, and has a pore size of approximately 2 to 10 microns, and said sensing electrode is approximately 0.050 inch in diameter.

2. An electrochemical gas sensor as set forth in claim 1, wherein:

said sheet of porous material is of polytetrafluoroethylene (PTFE);

and said sensing electrode is formed by pressing powdered platinum onto the inner surface of said sheet.

3. An improved electrochemical gas sensor having a sensor body with a hollow interior, an electrolyte filling the body, a sensing electrode, a counter electrode disposed at one end of the interior of said body, and a pair of wires making contact with the two electrodes, wherein the improvement comprises:

a sheet of relatively thick porous material forming a closure at the other end of the interior of the body, and having an inner surface in contact with the electrolyte and an outer surface that is exposed to a gas sample for analysis; and making the sensing electrode in the form of a relatively small area of powdered metal impregnated into the inner surface of said sheet by the application of pressure;

whereby said porous sheet ensures that gas diffuses into said electrolyte rapidly enough to yield insensitivity to temperature and a rapid response to pressure changes, but the relatively small area of said sensing electrode results in a relatively small electrical current and a correspondingly long, useful life;

and wherein said sheet of porous material is approximately 0.050 to 0.060 inch thick, approximately 0.5 inch in diameter, and has a pore size of approximately 2 to 10 microns, and said sensing electrode is approximately 0.050 inch in diameter.

4. An electrochemical gas sensor as set forth in claim 3, wherein:

said sheet of porous material is of polytetrafluoroethylene (PTFE);

and said sensing electrode is formed by pressing powdered platinum onto the inner surface of said sheet.

5. An electrochemical gas sensor, comprising:

a generally cylindrical sensor body with a hollow interior;

an electrolyte filling said body;

a counter electrode disposed at one end of the interior of said body;

a contact sheet closing said body and in electrical contact with said counter electrode;

a sheet of porous polytetrafluoroethylene (PTFE) material forming a closure at the other end of the interior of said body, and having an inner surface in contact with said electrolyte and an outer surface exposed to a gas sample for analysis;

a sensing electrode in the form of a relatively small area of powdered platinum impregnated into the inner surface of said sheet by the application of pressure; and a pair of wires for making contact with said sensing electrode and said counter electrode, respectively, to measure a current between said electrodes generated as a result of the diffusion of gas through said porous sheet;

whereby said porous PTFE sheet ensures that gas diffuses into said electrolyte rapidly enough to result in relative insensitivity to temperature and a rapid response to pressure changes, but the relatively small area of said sensing electrode results in a small electrical current and a correspondingly long useful life;

and wherein said sheet of porous PTFE material is approximately 0.5 inch in diameter, and has a pore size of approximately 2 to 10 microns, and said sensing electrode is approximately 0.050 inch in diameter.

* * * * *